United States Patent
Johnson et al.

(10) Patent No.: US 6,351,547 B1
(45) Date of Patent: Feb. 26, 2002

(54) METHOD AND APPARATUS FOR FORMATTING DIGITAL IMAGES TO CONFORM TO COMMUNICATIONS STANDARD

(75) Inventors: Chandler A. Johnson, Oconomowoc; Charles C. Brackett, Waukesha; Gregory C. Stratton, Wauwatosa; James S. Lehouillier, Waukesha; Takao Shiibashi, Brookfield, all of WI (US)

(73) Assignee: General Electric Company, Waukesha, WI (US)

( * ) Notice: Subject to any disclaimer, the term of this patent is extended or adjusted under 35 U.S.C. 154(b) by 0 days.

(21) Appl. No.: 09/300,966

(22) Filed: Apr. 28, 1999

(51) Int. Cl.[7] .................................................. G06K 9/00
(52) U.S. Cl. ........................ 382/128; 709/213; 709/219; 709/221; 709/223; 709/236; 709/312
(58) Field of Search .............................. 382/100, 128, 382/232; 367/7, 11; 709/200, 203, 213, 217, 219, 220, 221, 228, 236, 246, 247, 249, 312, 315, 316, 327, 330, 332; 707/104.1, 1, 3, 4, 10

(56) References Cited

U.S. PATENT DOCUMENTS

| | | | | |
|---|---|---|---|---|
| 4,853,875 A | * | 8/1989 | Brown ......................... | 709/228 |
| 5,321,520 A | * | 6/1994 | Inga et al. ................... | 358/403 |
| 5,655,084 A | * | 8/1997 | Pinsky et al. ................... | 705/3 |
| 5,740,267 A | * | 4/1998 | Echerer et al. ............. | 382/132 |
| 5,835,735 A | * | 11/1998 | Mason et al. ................ | 710/107 |
| 5,877,819 A | * | 3/1999 | Branson ...................... | 348/701 |
| 5,897,498 A | | 4/1999 | Canfield et al. ............ | 600/437 |
| 5,949,491 A | * | 9/1999 | Callahan et al. ............ | 348/442 |
| 5,950,207 A | * | 9/1999 | Mortimore et al. ......... | 707/104 |
| 5,971,923 A | * | 10/1999 | Finger ......................... | 600/437 |
| 6,213,945 B1 | * | 4/2001 | Tynan ......................... | 600/441 |
| 6,253,214 B1 | * | 6/2001 | Hall et al. .................... | 707/204 |
| 6,260,021 B1 | * | 7/2001 | Wong et al. ................... | 705/2 |
| 6,275,869 B1 | * | 8/2001 | Sieffert et al. .............. | 709/321 |

* cited by examiner

*Primary Examiner*—Andrew W. Johns
*Assistant Examiner*—Shervin Nakhjavan
(74) *Attorney, Agent, or Firm*—Peter J. Vogel; Dennis M. Flaherty

(57) ABSTRACT

A computerized imager is programmed with software that allows properly formatted image files (data objects) to be sent to multiple remotely located devices via a network. The imager is programmed with multiple configurable DICOM tasks, one task for each configured remote device. Each task is configured to format image files into DICOM objects acceptable to a particular remote device. Each DICOM object is constructed from image frame data and attribute data. Each DICOM task queries an Attribute Control Engine, which instructs that DICOM task concerning which attributes and what attribute values to include in the DICOM objects being constructed by that task. The Attribute Control Engine in turn reads the attribute information from an Attribute Control File. A respective Attribute Control file is provided for each configured remote device.

20 Claims, 8 Drawing Sheets

DEVICE CONFIGURATION PAGE 1 of 11

| | | | |
|---|---|---|---|
| NAME | PRINTER A | | |
| IP ADDR | 0 . 0 . 0 . 0 | AE TITLE | |
| PORT | 104 | COLOR COLOR | DEVICE TYPE PRINTER — 67 |
| RETRIES | 1 | RETRY INTERVAL 10 SEC | TIMEOUT 10 SEC |
| ECHO | ECHO ON | ACTIVATE YES — 66 | |

PRINTER SETUP

| | | | |
|---|---|---|---|
| FORMAT | 3 X 5 — 65 | ORIENTATION | PORTRAIT |
| SIZE | 8in x 10in | MEDIA TYPE | PAPER |
| COPIES | 1 | BORDER | BLACK |
| PRIORITY | HIGH | EMPTY | BLACK |
| MIN DENSITY | 0 | MAX DENSITY | 0 |
| TRIM | NO | DESTINATION | MAGAZINE |
| MAGNIFICATION | REPLICATE | | |
| SMOOTH | NONE | | |
| FILM SESSION LABEL | | | |

CONFIGURATION STRING

WORKLIST SETUP
POLLING RATE  0 MINUTES

STORAGE SETUP
TYPE  AUTOMATIC
LIVE IMAGING  OFF

TKBL/RET TO POSITION    SET TO SELECT    ROI   SIZE TO PAGE
                                         EXIT TO SAVE

PAGE 5 OF 6
STATUS

FRAMES: 100/297
FRAMES: 238/705

| | DEVICE CONTROL | | | |
|---|---|---|---|---|
| | P1 | P2 | SP1 | SP2 TYPE |

LOCAL STORAGE
 COLOR
 GRAY
 HARD DISK
 MOD

DICOM DEVICES
 PRINTER A
 PRINTER B
 STORAGE A

78

TKBL/RET TO POSITION    SET TO SELECT    ROI SIZE TO PAGE
                                          EXIT TO SAVE

FIG. 8

DEVICE ACTIVATION

| | NAME | ACTIVE |
|---|---|---|
| 1 | PRINTER A | YES —100 |
| 2 | PRINTER B | YES |
| 3 | STORAGE A | YES |
| 4 | STORAGE B | NO |
| 5 | PRINTER X | NO |
| 6 | PRINTER Y | NO |
| 7 | | NO |
| 8 | | NO |
| 9 | | NO |
| 10 | | NO |
| 11 | | NO |
| 12 | | NO |
| 13 | | NO |
| 14 | | NO |
| 15 | | NO |
| 16 | | NO |
| 17 | | NO |
| 18 | | NO |
| 19 | | NO |
| 20 | | NO |

TKBL/RET TO POSITION  SET TO SELECT  ROI SIZE TO PAGE
                                     EXIT TO SAVE

METHOD AND APPARATUS FOR FORMATTING DIGITAL IMAGES TO CONFORM TO COMMUNICATIONS STANDARD

FIELD OF THE INVENTION

This invention generally relates to imaging systems used in medical diagnostics. In particular, the invention relates to the transfer of digital images from an ultrasound imaging system over a network to remote devices for archiving and/or printing.

BACKGROUND OF THE INVENTION

Conventional ultrasound imagers create two-dimensional images of biological tissue by scanning a focused ultrasound beam in a scan plane and for each transmitted beam, detecting the ultrasound wave energy returned along a respective scan line in the scan plane. A single scan line (or small localized group of scan lines) is acquired by transmitting focused ultrasound energy at a point, and then receiving the reflected energy over time. The focused transmit energy is referred to as a transmit beam. During the time after transmit, one or more receive beamformers coherently sum the energy received by each channel, with dynamically changing phase rotation or delays, to produce peak sensitivity along the desired scan lines at ranges proportional to the elapsed time. The resulting focused sensitivity pattern is referred to as a receive beam. A scan line's resolution is a result of the directivity of the associated transmit and receive beam pair.

A B-mode ultrasound image is composed of multiple image scan lines. The brightness of a pixel on the display screen is based on the intensity of the echo returned from the biological tissue being scanned. The outputs of the receive beamformer channels are coherently summed to form a respective pixel intensity value for each sample volume in the object region or volume of interest. These pixel intensity values are log-compressed, scan-converted and then displayed as a B-mode image of the anatomy being scanned.

If the ultrasound probe is swept over an area of body, a succession of image frames (corresponding to spaced slices intersecting the body being examined) can be displayed on the monitor. In one type of ultrasound imaging system, a long sequence of the most recent images are stored and continuously updated automatically in a cine memory on a first-in, first-out basis. The cine memory is like a circular image buffer that runs in the background, capturing image data that is displayed in real time to the user. The cine memory acts as a buffer for transfer of images to digital archival devices via the host computer. When the user freezes the system (by operation of an appropriate device on an operator interface), the user has the capability to view image data previously captured in cine memory. The image loop stored in cine memory can be reviewed on the display monitor via trackball control incorporated in the operator interface, and a section of the image loop can be selected for hard disk storage.

If the transducer probe was moving during image acquisition, the succession of image frames stored in cine memory form a three-dimensional data volume of image information. This data volume can be used by the system computer to project a three-dimensional view of the area of interest. This projected image can be returned to memory and then displayed on the monitor. Any acquired or projected image can be stored internally on the system hard disk or on a magneto-optical disk (MOD) inserted in a disk drive.

In addition to storing images internally, modern ultrasound imaging systems need to be able to transfer images to various types of remote devices via a communications network. To successfully transfer images, the relevant networking features of the ultrasound imager must be compatible with the networking features of the destination remote device. In particular, the ultrasound imager must place the data to be transferred in a format which can be handled by the destination remote device. An attempt to accomplish the foregoing is the adoption of the DICOM (Digital Imaging and Communications in Medicine) standards, which specify the conformance requirements for the relevant networking features. The DICOM standards are intended for use in communicating medical digital images among printers, workstations, acquisition modules (such as an ultrasound imaging system) and file servers. The acquisition module is programmed to transfer data in a format which complies with the DICOM standards, while the receiving device is programmed to receive data which has been formatted in compliance with those same DICOM standards.

DICOM involves more than digital image transfer. DICOM functionality includes the following Service Classes: archive/transfer images: store (across network); archive/interchange images: media storage; query for information and retrieve images; make image hard copies: print management; patient, study and results management; radiology information system modality: worklist management; and test connectivity: verification. A fundamental concept employed in DICOM is "Services on Objects". One example of an "Object" is an ultrasound image. Two examples of a "Service" are the "Store" and "Query/Retrieve" functions. In DICOM, methods of operating on information objects are referred to as "Service Object Pair Classes" (SOP Classes). Examples of SOP Classes are "Store an ultrasound image", "Print an ultrasound image", "Find which studies there are for a certain patient", "Retrieve all studies of a certain patient" and "Retrieve a worklist". Unique Identifiers (UIDs) are defined for all SOP Classes. UIDs are also given to all studies, series and images. These UIDs are, for instance, used for retrieval. In the DICOM vernacular, a patient has a study which comprises a study component, e.g., examination using a particular modality. Images acquired in sequence in the course of a study on a patient form a series of objects.

The DICOM system is based on the client/server concept. The device which uses a service (on objects) is the client device, while the device which provides the service is the server device. The client device is referred to as a Service Class User (SCU), while the server device is referred to as a Service Class Provider (SCP). The SCU sends a Service Request to the SCP over a local area network (LAN). The SCP sends back a response to the SCU over the same LAN. If the response is affirmative and a communications syntax is agreed upon, an association between the SCU and the SCP is opened and data can be transferred between the two devices. In the DICOM system a device is not limited to one role: it can be both SCU and SCP at different times.

The DICOM system is designed to facilitate the communication of digital images of different types, e.g., X-ray, computerized tomography, magnetic resonance and ultrasound imaging. In an ultrasound imager having conventional DICOM capability, three local real-world activities occur: Image Send, Image Print and Remote Verification. Image Send and Image Print can be done in either automatic or manual mode. Verification of remote DICOM devices configured on the ultrasound imager is performed when the imager is powered up or when requested by the system operator.

All DICOM activities are handled in a queued manner by application software running on a host computer incorporated in the imager. In one type of ultrasound imager, the user can select any image in cine memory to be sent in DICOM format via a LAN to a remote device having DICOM capability. The host computer of the ultrasound imaging system is programmed with DICOM system software which facilitates transmission of image frames from the cine memory to the remote DICOM device via the host computer hard disk and the LAN.

In the conventional ultrasound imager, Image Send can be used in automatic or manual mode, depending on the user configuration. When automatic mode is configured, console keys are used to capture the image and to store it on the hard disk. The request is queued to a DICOM queue manager (preferably implemented in software), which requests an association with the destination remote device. After the association with the remote device has been opened, the queue manager "pushes" the image to the remote device without user intervention. The transfer is done in the background while scanning or other operator activities continue. In manual mode, the captured images are archived on the hard disk or on a MOD during the exam(s). Upon completion of the exam(s) the images are tagged using an archive menu and queued to any of the network devices that have been configured on the imager. The images are sent sequentially in the background while scanning or other operator activities proceed. Image Print works much the same way as Image Send, in both automatic and manual modes, the only difference being that the destination device is a printer.

In order to accomplish image transfer, the ultrasound imaging system must know the configuration of the destination remote device prior to attempting to communicate with that device. The configuration data for the destination remote device is typically inputted to the ultrasound imager during software installation by a field engineer, although the DICOM network can be configured at any time. When the imager receives an instruction to transmit data to a particular remote device from the system operator, the imager software converts the image data to be transferred into the DICOM format required by the destination remote device, based on the configuration data for that device stored in system memory. The imager also sends a request over the network to the destination remote device to open an association, i.e., to connect the imager to the destination remote device. If the remote device responds in the affirmative, the imager and remote device then agree on which SOP Class is to be used and which device will act as the server and which as the client. The ultrasound imager also selects the appropriate encoding syntax from those accepted by the remote device. Other communication parameters are also negotiated.

After the DICOM communications protocol has been settled, the association is opened and the imager attempts to send the DICOM-formatted image file (object) to the remote device via the network. The transfer is done in the background while scanning or other operator activities continue. If the remote device is a storage device, each image file is transferred singly in response to a Send request inputted by the operator. The conventional imager with DICOM capability will open an association with a storage device in response to each "send to a storage device" instruction. If a transfer is successful, the association for that transfer is immediately closed. If the remote device is a printer configured to print multi-image film, then a number of images are accumulated to make up a multi-image film and an association is opened in response to a Send instruction when a number of images sufficient to fill the multi-image film have been accumulated. After the full film session of images has been transmitted, the association between the imager and printer is closed.

If the destination remote device sends back a message indicating successful receipt of the transmitted data, the DICOM-formatted image file can be deleted from the imager memory. Alternatively, the system operator can instruct the imager to retain the DICOM-formatted image file on the imager hard disk or to store it on a MOD inserted in the imager.

The remote device to which the ultrasound imager sends data can be a printer, a storage device or other device. If the operator interface of the imager has only one configurable Print/Store button, then that button will be configured to initiate data transfer to the destination remote device. The configuration data for the remote device will indicate the type of device to the imager and then the imager will format the data being transferred accordingly. If the operator interface has multiple Print/Store buttons, then each button can be configured to initiate data transfer to a respective remote device. Data transfer to any one of those configured remote devices can then be initiated by pressing the appropriate Print/Store button.

In addition to the digitized image (i.e., pixel data), the DICOM object transferred from the ultrasound imager also includes attribute information. For example, the attribute information may include patient attributes (e.g., patient name and patient identification number), study attributes (e.g., accession number and study date), series attributes (e.g., modality type and series date), and image attributes (e.g., image type and numbers of rows and columns). Each attribute has a name, a value representation and a tag. A tag is a number unique to the attribute. The value representation defines what type of value the attribute can have (e.g., a 64-character string, binary data, etc.).

In accordance with DICOM standards, there are three types of attributes. Type 1 comprises attributes which are mandatory and must always be present with a value; Type 2 comprises attributes which are mandatory but are allowed to be empty; and Type 3 comprises attributes which are optional and are also allowed to be empty. An incompatibility between two devices may arise, for example, if the receiving device requires that a Type 3 attribute be transmitted while the sending device does not include that attribute in its transmission. As a result, even if both devices are configured in accordance with current DICOM standards, the data transfer cannot occur. Thus, even mutual conformance to DICOM standards does not guarantee that two devices can be compatibly connected to each other.

In accordance with a further aspect of the DICOM system as currently implemented, an ultrasound imaging system can retrieve a worklist from a Radiology Information System (RIS) at a hospital via the LAN. The retrieved worklist may, e.g., comprise all patients to be examined on a particular day using that particular ultrasound imager. The worklist includes the following information for each patient: name, identification number, sex, birth date, accession number, study data, etc. The information retrieval is initiated by the ultrasound imager. In response to this query, the RIS transmits the worklist to the ultrasound imager, which stores it in memory. This worklist is then available for viewing by the sonographer. The patient currently being examined can be selected from the worklist.

Because the DICOM capability is implemented in software, these features of the ultrasound imaging system can be readily upgraded. One goal of such upgrades is to increase the efficiency of the system operator by making the system simpler to operate, e.g., by requiring fewer manipulations to activate a particular operation. Another goal of system upgrades is to increase the ability of the imager to connect rapidly, efficiently and reliably to remote devices on the network, i.e., to increase connectivity.

In one commercially available ultrasound imager having DICOM capability, the imager is programmed with seven DICOM tasks, each of which is dedicated to a specific type of device, e.g., four printer tasks, two storage tasks and one worklist task. These dedicated tasks are set upon system power up and cannot be altered by the system user, e.g., the printer tasks cannot be changed to storage tasks and vice versa. In addition, each imager has a single hard-coded Attribute Control File which cannot be changed. Accordingly, if a particular remote device requires an attribute which is absent from the hard-coded Attribute Control File, the imaging system will be unable to send images to that particular remote device via the DICOM network.

SUMMARY OF THE INVENTION

The present invention is incorporated in an imager which is programmed with multiple DICOM tasks, all but one of these DICOM tasks being configurable by the user to be either a storage task or a printer task. Each DICOM task can be configured by entries on a respective page of an operator-interactive device configuration menu. Each configured remote device can be "activated" by clicking on an activation field on a respective page of the same menu. In the preferred embodiment, "clicking" is accomplished by manipulating a trackball to highlight a desired field and then pressing the Set key on the keyboard. In response to "activation", a respective DICOM task will be configured to the remote device associated with that menu page in accordance with the configuration data entered on that page. It should be appreciated that the term "activation", as used in this context, means that the imager has a DICOM task configured for that device, not that the remote device itself is in any sense remotely activated by the imager.

In particular, each page of the device configuration menu has a field for identifying the type of remote device. In response to activation of each device, a corresponding DICOM task is configured to convert image files into print objects or storage objects, depending on the type of remote device identified. In accordance with the DICOM standard, each DICOM task is designed to convert an image file, comprising image frame data and attribute data, into a DICOM-formatted object, also comprising image frame and attribute data. That DICOM object must conform not only to the DICOM standards, but also to the attribute requirements of the remote device destined to receive that DICOM object.

In accordance with the preferred embodiment of the present invention, each DICOM task constructs DICOM objects by incorporating attribute data derived from a so-called Attribute Control File. Each DICOM task has a respective Attribute Control File associated therewith. The respective Attribute Control File in turn contains a mapping of all attributes which need to be included in the DICOM objects destined for a respective remote device. Thus, each configured and activated remote device has both a respective DICOM task and a respective Attribute Control File associated therewith.

Initially, the imaging system imaging system is provided with a multiplicity of identical Attribute Control Files. If the number of DICOM tasks is N, then (N+1) identical Attribute Control Files are stored on the hard disk. The first N Attribute Control Files are programmable; the (N+1)-th Attribute Control File is read only and serves as the default Attribute Control File.

In the event that communication with a particular remote device is not possible due to an incompatibility between the unmodified imaging system Attribute Control File and that remote device's attribute requirements, a service engineer can reprogram the particular Attribute Control File to conform to those requirements. The default Attribute Control File is used as the standard for a service engineer to copy if any of the programmable Attribute Control Files need to be reset to factory default.

Each Attribute Control File, in ASCII format, is a mapping of which attributes should be associated with every image sent to the remote device associated with that Attribute Control File. Each DICOM task will convert each image file into a DICOM object having the acquired image data from the image file as well as the attribute data dictated by the Attribute Control File associated with that DICOM task. The data for a particular attribute may be taken from either the image file or from the Attribute Control File during construction of the DICOM object by the DICOM task.

In accordance with a further feature of the preferred embodiment, the host computer is programmed with an Attribute Control Engine which controls the inclusion of particular attributes and attribute values in the DICOM objects constructed by each DICOM task. In particular, in response to queries from a DICOM task, the Attribute Control Engine will instruct that DICOM task concerning which attributes and what attributes values should be included in the DICOM object being constructed. The Attribute Control Engine in turn obtains that information from the Attribute Control File associated with that DICOM task.

The invention disclosed herein relates generally to imaging systems which acquire images that need to be sent to remotely located devices via a network. Although the disclosed preferred embodiment is an ultrasound imaging system, the invention has application in other types of imaging systems. Furthermore, although the preferred embodiment of the invention communicates with remote devices using the DICOM standard, the invention has application with any digital image communications standard or protocol.

BRIEF DESCRIPTION OF THE DRAWINGS

FIG. 4 is a schematic reproducing a "Device Configuration" menu which can be called up on the display monitor during configuration of the imaging system in accordance with the preferred embodiment.

FIG. 6 is a schematic reproducing a "Device Control" menu which can be used to configure the Print/Store buttons on the operator interface in accordance with the preferred embodiment.

FIG. 8 is a schematic reproducing a "Device Activation" menu which can be used to activate selected configured remote devices in accordance with the preferred embodiment.

DETAILED DESCRIPTION OF THE PREFERRED EMBODIMENTS

Figure 1:
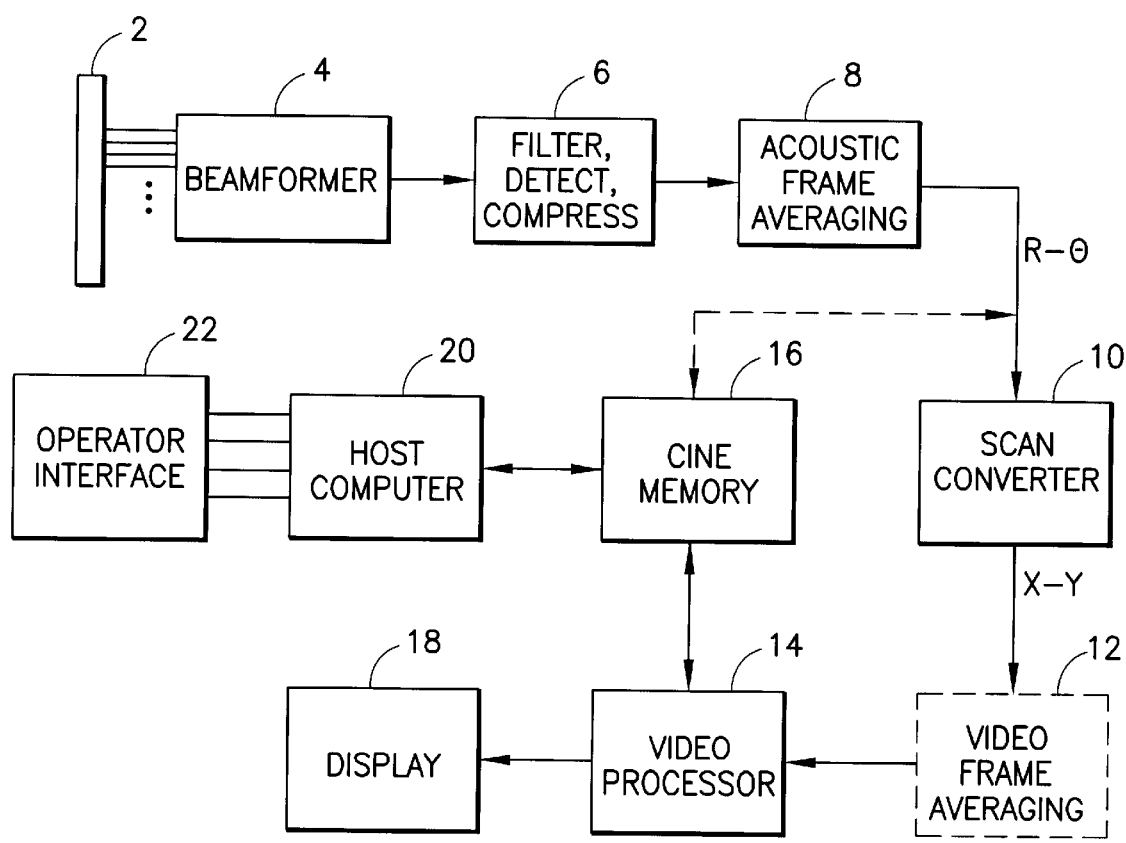
FIG. 1 is a block diagram showing a conventional ultrasound imaging system of the type which can be programmed to have DICOM capability.

FIG. 1 shows a conventional computerized ultrasound imaging system which can be programmed to communicate with remote devices over a network in conformance with the DICOM standard. The type of imaging system depicted in FIG. 1 creates two-dimensional B-mode images of tissue in which the brightness of a pixel is based on the intensity of the echo return. The basic signal processing chain is as follows.

An ultrasound transducer array 2 is activated to by a transmitter in a beamformer 4 to transmit an acoustic burst which is focused at a point along a scan line. The return RF signals are detected by the transducer elements and then dynamically focused to form a receive beam by a receiver in the beamformer 4. The receive beamformer output data (I/Q or RF) for each scan line is passed through a B-mode processing chain 6, which preferably includes demodulation, filtering, envelope detection, logarithmic compression and edge enhancement.

Depending on the scan geometry, up to a few hundred receive vectors may be used to form a single acoustic image frame. To smooth the temporal transition from one acoustic frame to the next, some acoustic frame averaging 8 may be performed before scan conversion. In general, the log-compressed display data is converted by the scan converter 10 into X-Y format for video display. On some systems, frame averaging may be performed on the X-Y data (indicated by dashed block 12) rather than the acoustic frames before scan conversion, and sometimes duplicate video frames may be inserted between acoustic frames in order to achieve a given video display frame rate. The scan-converted frames are passed to a video processor 14, which maps the video data using a gray-scale mapping. The gray-scaled image frames are then sent to a video monitor 18 for display.

System control is centered in a host computer 20, which accepts operator inputs through an operator interface 22 and in turn controls the various sub-systems. (In FIG. 1, only the image data transfer paths are depicted.) The operator interface comprises a keyboard, a trackball, a multiplicity of push-buttons, and other input devices such as sliding and rotary knobs.

During imaging, a long sequence of the most recent images are stored and continuously updated automatically in a cine memory 16. Some systems are designed to save the R-θ acoustic images (this data path is indicated by the dashed line in FIG. 1), while other systems store the X-Y video images. The image loop stored in cine memory 16 can be reviewed via trackball control, and a section of the image loop can be selected for hard disk storage.

For an ultrasound imaging system which has been configured with a free-hand three-dimensional imaging capability, the selected image sequence stored in cine memory 16 is transferred to the host computer 20 for three-dimensional reconstruction. The result is written back into another portion of the cine memory, from where it is sent to the display system 18 via video processor 14.

Figure 2:
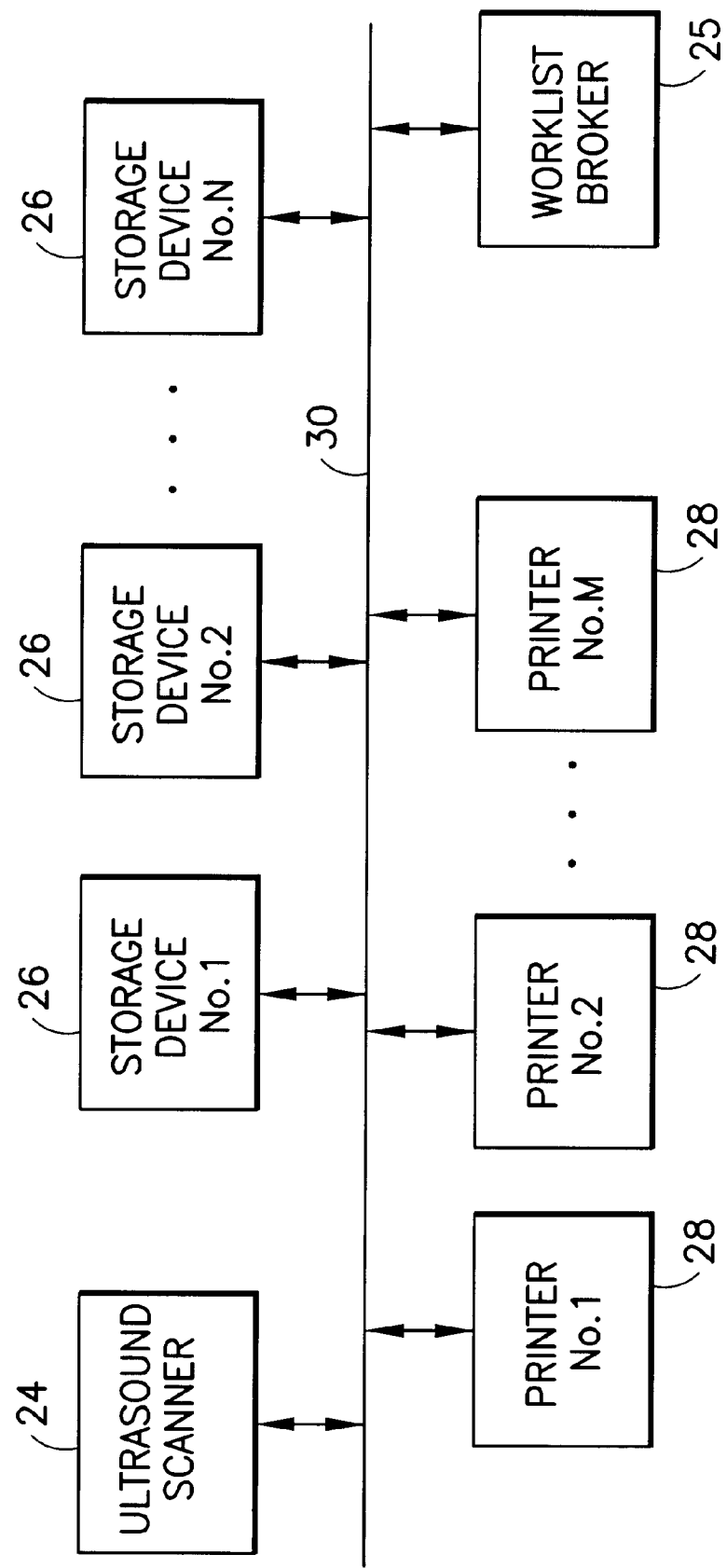
FIG. 2 is a block diagram showing a typical DICOM network.

FIG. 2 generally depicts a simplified DICOM network having an ultrasound scanner 24, a worklist broker (e.g., an RIS) 25, N storage devices 26, and M printing devices 28, all connected to a LAN 30. It will be readily appreciated that this diagram represents a simplified example of a DICOM network and that an actual DICOM network in the real world will have many more devices connected to the LAN, including modalities other than ultrasound imaging systems. The present invention is incorporated in an ultrasound imager (scanner) having the built-in capability to communicate with any one or more of the devices 25, 26 and 28 in conformance with the DICOM requirements.

Figure 3:
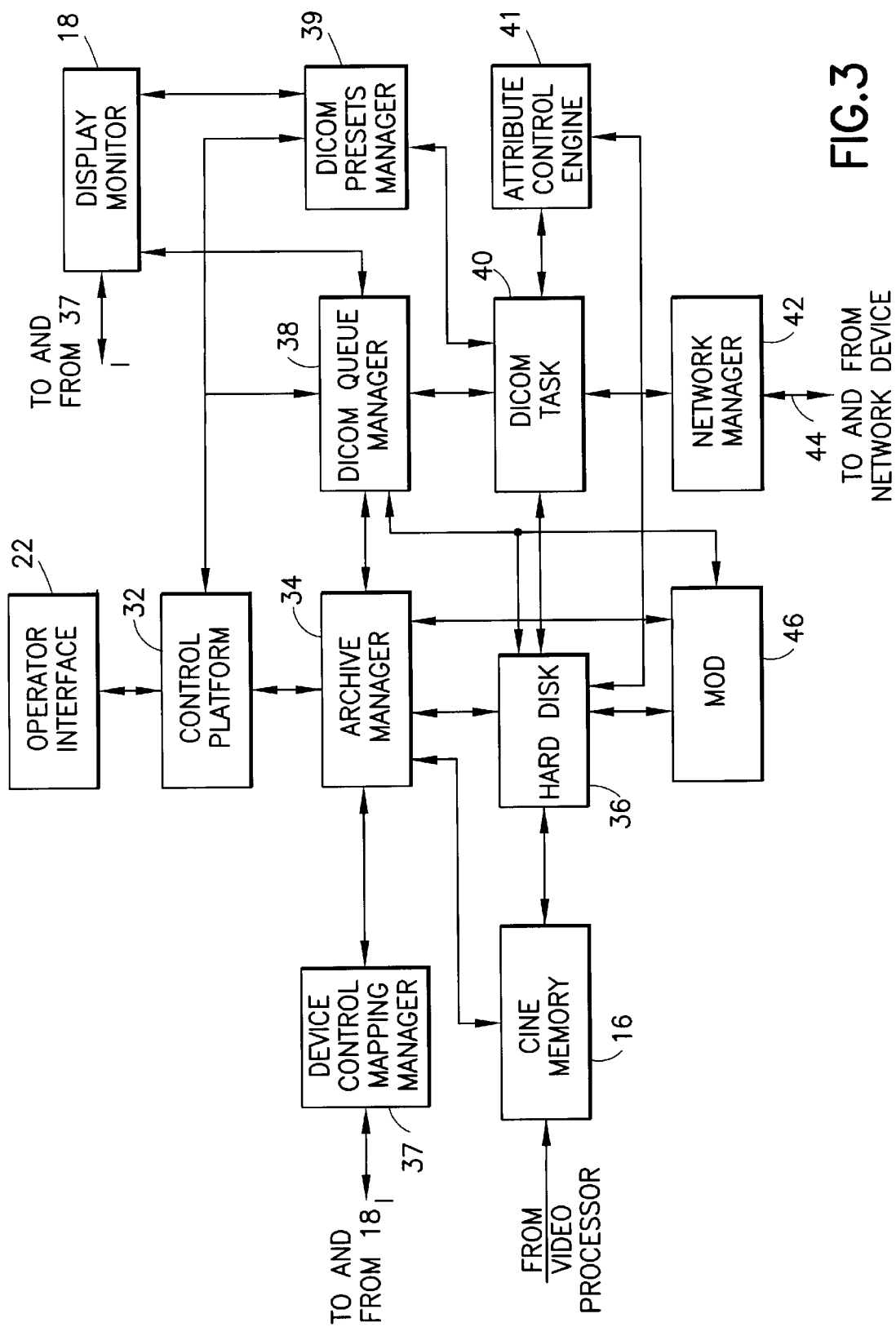
FIG. 3 is a block diagram generally depicting the hardware and software of an ultrasound imaging system in accordance with the preferred embodiment.

A portion of such an ultrasound imager is generally depicted in FIG. 3. At the outset it should be appreciated that all of the blocks depicted in FIG. 3, with the exceptions of the cine memory 16, the display monitor 18 and the operator interface 22, are preferably incorporated in the host computer (depicted in FIG. 1 as block 20). It should be further appreciated that blocks 32, 34, and 37–42 in FIG. 3 are preferably implemented as software.

In the system depicted in FIG. 3, commands inputted via the operator interface 22 are detected and processed by a control platform 32. In return, the control platform will provide signals to the operator interface which activate various visual indicators on the operator interface to indicate the status of various functions. In response to manipulation of the appropriate key or appropriate set of keys by the operator, the DICOM presets manager 39 will display a "Device Configuration" menu (shown in FIG. 4) on the display monitor 18. The operator then enters configuration data for the first destination remote device (e.g., "Printer A" in FIG. 4) via the operator interface. Depending on whether the device being configured is a printer or storage device, the Device Type field 67 on the Device Configuration menu will be filled in with either a "Printer" or a "Storage" entry. If the device being configured is a printer which prints multi-image film sessions, then the Format field 65 in the "Printer Setup" section on the Device Configuration menu will be filled in with numbers indicating the printing format of the multi-image printer (e.g., "3×5" in the case of Printer A). For single-image printers, the entry in Format field 65 will be "1×1". A separate page of the "Device Configuration" menu will be "filled in" for each remote device which the operator wishes to configure.

The imager shown in FIG. 3 is designed to communicate with a configured remote device only if that device has been "activated". Activation causes the DICOM presets manager 39 to configure one of a multiplicity of DICOM tasks 40 in accordance with configuration data entered into the system for the associated remote device. That particular DICOM task will thereafter remain configured for that type of remote device until reconfigured for a different device. Other DICOM tasks are configured for other remote devices.

One way of activating a remote device is to click on the Activate field 66 on the Device Configuration menu to toggle the "Activate" state on. A second click on field 66 will toggle the "Activate" state off, and so forth. Alternatively, the operator can call up the Device Activation menu shown in FIG. 8, which is sent to the display monitor by the DICOM presets manager 39. The Device Activation menu comprises a list of the names of all configured remote devices, whether activated or not. A respective Activation field 100 is associated with each named device. Each Activation field 100 is a virtual representation of an Activation toggle switch. In other words, the imager is programmed with software which allows the user to activate and de-activate each configured device by simply clicking on its associated Activation field. A Yes or No is displayed in the Activation field to provide a visual indication of whether the remote device is activated.

Each activated remote device will be listed on the DICOM status menu (shown in FIG. 5) and on the Device Control menu (shown in FIG. 6). These menus are respectively sent to the display monitor by the DICOM queue manager 38 and the device control mapping manager 37. The following description assumes that the remote devices named Printer A, Printer B and Storage A have been configured and activated, while the remote devices named Printer X, Printer Y and Storage B have been configured and not activated (see FIG. 8).

Referring again to FIG. 3, the preferred embodiment is equipped with a plurality of Print/Store buttons on the operator interface 22. Each Print/Store button can be configured by the device control mapping manager 37 to initiate image transfer to more than one remote device, e.g., when a particular Print/Store button is pressed, the computer will send the corresponding acquired image to all activated remote devices configured for that button. The device control mapping manager is programmed to retrieve a Device Control menu, which is a virtual representation of the various configurations for the Print/Store buttons, from the hard disk 36 and send it to the display monitor 18. An exemplary Device Control menu for an imager having the functional equivalent of four Print/Store buttons, P1, P2, SP1 and SP2, is shown in FIG. 6. The P1 and P2 control states are respectively activated by pressing buttons P1 and P2 on the operator interface; the SP1 and SP2 control states are respectively activated by pressing buttons P1 and P2 while the Shift key is also depressed. Each of these four control states in turn can be configured so that the data of the acquired image is expressed as either color intensity values or gray-scale intensity values; so that the acquired image will be stored on the hard disk or the MOD; so that the acquired image will be transferred to one or more activated remote devices (e.g., Printers A and B and Storage A denoted in FIG. 6); or any combination of these options. For example, the imager represented in FIG. 6 is configured as follows: a color image will be transferred to Printer A and Storage A subsequent to depression of button P1; a gray-scale image will be transferred to Printer A and Storage A subsequent to depression of button P2 and the Shift key; a gray-scale image will be stored on the hard disk subsequent to depression of button P2; and a gray-scale image will be transferred to Printer B subsequent to depression of button P1 and the Shift key. Each Print/Store button configuration can be set via the operator interface. Any one of the device control fields 78 can be set by highlighting that field using the trackball and then pressing the Set key. The particular configuration of each Print/Store button is indicated by a symbol displayed in each set device control field. For each remote device ("DICOM Device" on the Device Control menu) configured to a particular Print/Store button, pressing that button after freezing an image will cause the associated DICOM task to retrieve an image file having a copy of that image from the hard disk and convert that image file to a DICOM object compatible with the associated remote device.

In accordance with the preferred embodiment, the device control mapping manager constructs a mapping of DICOM tasks (configured for respective remote devices) to Print/Store buttons. In other words, when the operator interacts with the Device Control menu (shown in FIG. 6) to configure a Print/Sore button to a particular remote device, the device control mapping manager then identifies the DICOM task corresponding to that remote device and includes it in the device control mapping. The device control mapping manager 37 provides the device control mapping to the archive manger 34. When the archive manager later receives a posting from the control platform 32 that a particular Print/Store button has been pressed, the archive manager 34 will then refer to the device control mapping and determine the DICOM tasks associated with that button from the mapping. The archive manager 34 then advises the DICOM queue manager 38 which DICOM tasks 40 need to construct objects incorporating the selected image frame. The DICOM queue manager 38 then copies that image file once for each task and, if the remote devices are storage devices or single-image printers, adds a job element to the Active Queue of each task. For multi-image printers, the DICOM queue manager 38 need only add another image file name to the Image File Name field of an existing job element in the queue.

Although FIG. 3 depicts only one DICOM task, in accordance with the preferred embodiment, the imager is programmed with multiple DICOM tasks. In the preferred embodiment, one DICOM task is dedicated to worklist management and ten DICOM tasks can be configured to convert image files into either DICOM print objects or DICOM storage objects. It should be appreciated, however, that the present invention is not restricted to having ten DICOM tasks for printing and storage. In response to pressing of a Print/Store button which is configured for multiple remote devices, a corresponding multiplicity of DICOM tasks will be started substantially simultaneously. These concurrently running tasks are performed using conventional multi-tasking principles.

In accordance with the preferred embodiment, the host computer of the imager is programmed to store in memory the configuration data input via the Device Configuration menu shown in FIG. 4. For each configured remote device which is activated, a respective DICOM task is configured by the DICOM presets manager 39 in accordance with the stored configuration data. In other words, each DICOM task is partly defined by the inputs to the corresponding page of the Device Configuration menu. In particular, each DICOM task is programmed to convert an image file into a print object for printers, if "Printer" was entered in the Device Type field 67 (see FIG. 4) on the Device configuration menu, and into a storage object for storage devices, if "Storage" was entered in the Device Type field. In the case where more than one remote device is designated to receive the same image, the associated DICOM tasks will convert respective copies of that image into respective DICOM objects acceptable to the respective remote devices.

At the beginning of every exam the system user (sonographer or monologist) pushes a "New Patient" button, causing a menu to appear on the screen of the display monitor. The user then enters information about the patient (e.g., name, patient identifier, accession number, birthdate, etc.). When data entry is completed, the user exits the menu. At this time, a DICOM Study Instance UID is created. This Study Instance UID forms the base of the SOP Instance UID which tells the receiving DICOM device (SCP) that the image received belongs to a particular patient. Every image taken by the user, after exiting the "New Patient" menu, will have the same UID.

The examination may then begin. The user will scan the patient as needed. The user, at any time, can freeze the image and take a snapshot of that image to send to a remote device. If the receiving device is a printer, the Instance UID is not of any concern. Printers may be configured to put more than one image on a piece of film (e.g., 3×5=15 images). If this were the case, the user would normally take all 15 images before sending the completed film session to the printer.

If the receiving device is a storage device, then the SOP Instance UID will direct the image to that patient's folder of images. Storage devices receive images one at a time. The typical method of image transfer to a storage device is as follows: the DICOM task opens an association (connection) with the receiving storage device; transfer negotiations occur; the image is transferred; and the association is closed. Alternatively, the imager can be configured to open the association once and keep it open throughout the entire exam. In the latter case, the association is opened upon the sending of the first image and is closed by pressing an "End Exam" key.

The image transfer procedure used in the preferred embodiment will be described in more detail with reference to FIG. 3. In response to a request from the operator to archive a frozen image, the control platform 32 sends an "Image Store" instruction to the archive manager 34. In response to the "Image Store" instruction, the archive manager retrieves the frozen image from cine memory 16 and stores it either on the hard disk 36 or on the MOD 46, depending on the system operator's selection.

In addition, the system operator may request that the frozen image be sent to an activated remote device for printing or storage by pressing the appropriate Print/Store button. In response to a request from the operator to transfer a frozen image to a remote device, the control platform 32 sends an "Image Send" instruction to the archive manager 34. The archive manager 34 retrieves the frozen image from the cine memory 16 and stores it in a file on the hard disk 36. The file includes the image pixel data as well as certain attribute data, such as patient name, patient ID, gray-scale or color image, number of rows and columns of pixels, etc. Then the archive manager 34 notifies the DICOM queue manager 38 of the image to be transferred and the destination remote device that image (and subsequent images of the same job) will go to. Next the queue manager 38 copies the image to another location on the hard disk and gives that copied image a new file name. If the pressed Print/Store button is configured for multiple remote devices, then the queue manager 38 will store multiple copies of the frozen image in multiple files, i.e., a separate copy of the frozen image for each remote device designated as a destination for that image.

In accordance with the DICOM standard, each DICOM task is designed to convert an image file, comprising image frame data and attribute data, into a DICOM-formatted object, also comprising image frame and attribute data. That DICOM object must conform not only to the DICOM standards, but also to the attribute requirements of the remote device destined to receive that DICOM object.

In accordance with the preferred embodiment of the present invention, each DICOM task 40 has a respective Attribute Control File associated therewith. The respective Attribute Control File in turn contains a mapping of all attributes which need to be included in the DICOM objects destined for a respective remote device. Initially, when the imaging system leaves the factory, the imaging system is provided with identical Attribute Control Files. If the number of DICOM tasks is N, then (N+1) identical Attribute Control Files are stored on the hard disk 36. The first N Attribute Control Files are programmable; the (N+1)-th Attribute Control File is read only and serves as the default Attribute Control File. In the event that communication with a particular remote device is not possible due to incompatibility between the unmodified imaging system Attribute Control File and that remote device's attribute requirements, a service engineer can reprogram the particular Attribute Control File to conform to those requirements. The default Attribute Control File is used as the standard for a service engineer to copy if any of the programmable Attribute Control Files need to be reset to factory default.

Each activated configured remote device has its own Attribute Control File. This file, in ASCII format, is a mapping of which attributes should be associated with every image sent to the remote device associated with that Attribute Control File. Each DICOM task will convert each image file into a DICOM object having the acquired image data from the image file as well as the attribute data dictated by the Attribute Control File associated with that DICOM task. The data for a particular attribute may be taken from either the image file or from the Attribute Control File during construction of the DICOM object by the DICOM task.

In accordance with a further feature of the preferred embodiment, the host computer is programmed with an Attribute Control Engine 41 which controls the inclusion of particular attributes and attribute values in the DICOM objects constructed by each DICOM task 40. When the system is powered up, the Attribute Control Engine 41 reads the N Attribute Control Files associated with the N DICOM print/storage tasks are read from the hard disk 36 and written into system memory. These Attribute Control Files are kept in system memory for the duration of the power cycle. Each Attribute Control File comprises many lines for setting up the DICOM attributes. One line is needed to set up one DICOM attribute. The format of each line is as follows:

[Module Name][Tag Number][Sequence Number] [Format String]

The module name specifies the DICOM module which the attribute on that line belongs to. The module name is a defined term. The tag number specifies a particular attribute included in that module. Some DICOM attributes have the sequence of the subset of some DICOM attributes. The sequence number specifies the sequence which the attribute belongs to. The format string specifies how the data of value of the attribute should be created.

Each DICOM task 40 must receive instructions from the Attribute Control Engine 41 concerning which attributes and attribute values should be included in the DICOM object being constructed by that DICOM task. First, the DICOM task 40 asks the Attribute Control Engine 41 whether a particular attribute should be included in the DICOM object. The Attribute Control Engine 41 refers to the associated Attribute Control File to determine whether the attribute should be included. If the attribute should not be included, the Attribute Control Engine 41 advises the DICOM task accordingly. The DICOM task 40 then proceeds to the next attribute. If the attribute should be included in the DICOM object under construction, the Attribute Control Engine 41 so advises the DICOM task 40. The DICOM task then asks the Attribute Control Engine 41 whether the value of that attribute should be obtained from the image file which is being converted or whether the attribute value should be obtained from the associated Attribute Control File. Again the Attribute Control Engine 41 refers to that associated Attribute Control File. If the attribute value should be taken from the image file, the Attribute Control Engine so advises the DICOM task. Alternatively, if the attribute value should be taken from the associated Attribute Control File, the Attribute Control Engine 41 retrieves that attribute value and sends it to the DICOM task 40.

The foregoing procedure is repeated for each attribute associated with the particular function, i.e., construction of a print object or storage object, being performed by the particular DICOM task. In other words, if the DICOM task is performing the storage function, then the DICOM task will query the Attribute Control Engine with regard to only those attributes which are relevant to the storage function. Likewise for the print function. In response to each query from the DICOM task 40 regarding a particular attribute, the Attribute Control Engine 41 will read only that line in the associated Attribute Control File corresponding to that attribute.

Referring still to FIG. 3, each DICOM task 40 sends its DICOM object in proper format to the corresponding destination remote device via the network manager 42 and the port 44. The DICOM tasks run concurrently and independently of each other in accordance with conventional multitasking principles.

Jobs which are waiting to be converted into DICOM objects by a DICOM task are queued. The queue is managed by a DICOM queue manager 38. Completed jobs awaiting conversion and transfer are held in a so-called Active Queue. For each job, the queue manager 38 adds a separate entry in the Active Queue. In particular, each entry comprises an element having multiple fields. One of those fields lists the image file names for the images in the particular job. Each image file name serves as a pointer for retrieval from memory of the named image. Another field in the element identifies the remote device (by identifying the Task ID of the DICOM task associated with that remote device) which that stored image is destined to be sent to.

Figure 7:
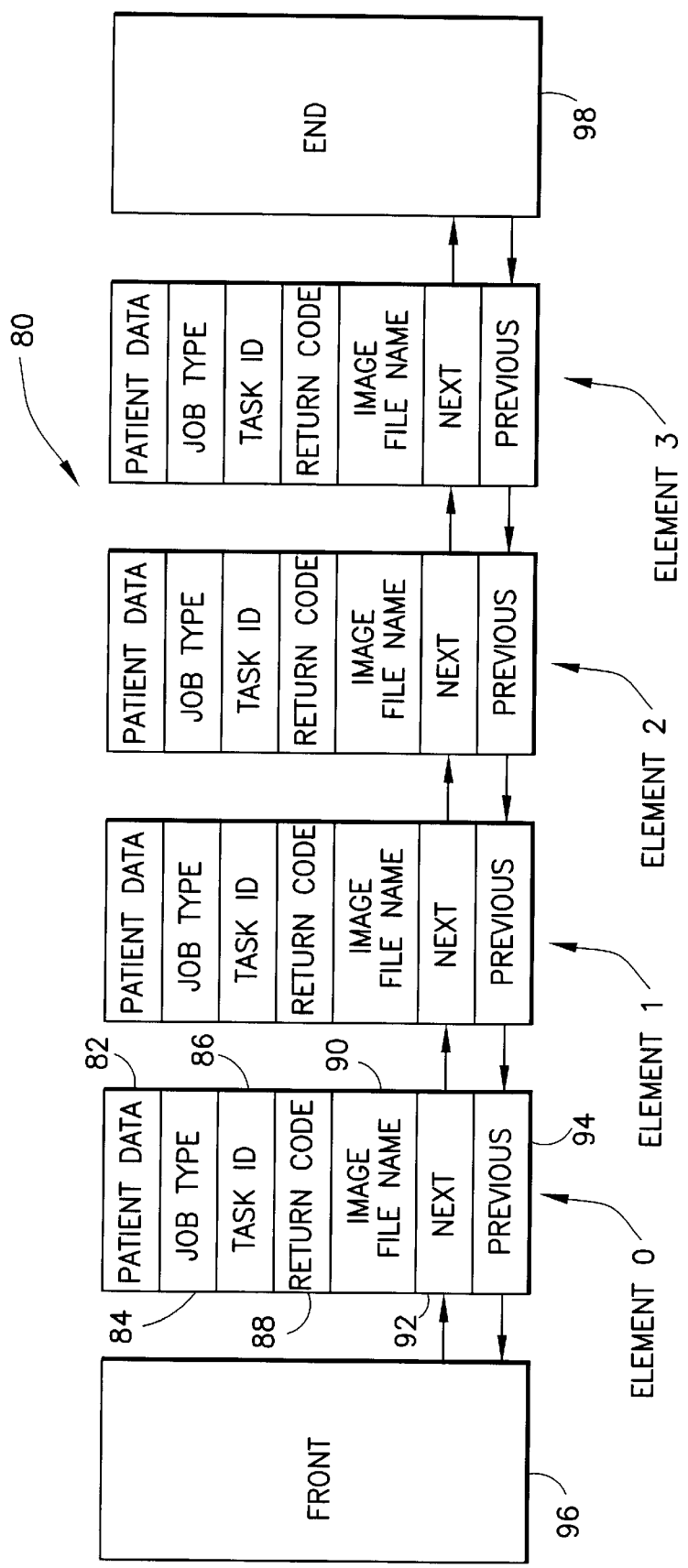
FIG. 7 is a schematic depicting a double-linked list stored in dynamically allocated memory space and serving as a job queue in accordance with the preferred embodiment.

The Active Queue, Partial Print Queue and Holding Queue are preferably double-linked lists of the type depicted in FIG. 7. List 80 comprises a plurality of linked elements (e.g., elements 0 through 3) which are stored in dynamically allocated memory space on the hard disk. The term "dynamically allocated", as used herein, means that the amount of memory space allocated to store a particular list is a function of the size of the list. In other words, as more elements, corresponding to additional tasks, are added to (removed from) the list, the amount of memory space allocated to store the list is correspondingly increased (decreased). Each element comprises a data structure 82 containing patient information (for use outside of the DICOM task); a data structure 84 containing information as to the job type (print or storage); a data structure 86 containing the task ID (which is equivalent to an ID for the destination remote device, since each task corresponds to a respective destination remote device); a data structure 88 for the value representing a successful transfer to the destination remote device; a pointer 90 to the image file or files to be transferred by the identified task; a pointer 92 to the next element in the list; and a pointer 94 to the previous element in the list. The front and end of the list 80 are indicated by blocks 96 and 98 respectively.

If the remote device is a storage device or a printer which prints single images, an entry is added to the Active Queue for each image (job) selected for transfer to a remote device. If the remote device is a printer which prints multi-image film sessions, an entry is added to a Partial Print Queue for each job. The Partial Print Queue is also preferably a linked list of elements. Copies of the Active Queue and Partial Print Queue (as well as the Holding Queue referred to later) are stored on the hard disk 36. Entries can be added at any place on the linked list. The Next or Previous pointer of any element adjacent to an added or deleted element must be changed to take account of new adjacent elements.

The Partial Print Queue is constructed of elements identifying respective multi-image film sessions. The Job Type field 84 in each element indicates whether the Image File Name field 90 contains the names of multiple images associated with a particular printing job. For example, if images are to be transferred to a printer which is configured to print film sessions comprising N images, then the imager will normally not send each film session until all N images have been acquired. The Partial Print Queue will include an element for each job. Image file names will be added to the Image File Name field 90 as the first through (N–1)-th images are accumulated. When the N-th image has been accumulated and its name has been added to the Image File Name field, the entire element will be deleted from the Partial Print Queue and added to the Active Queue.

Referring again to FIG. 3, the first job in the Active Queue is sent by the queue manager 38 to the DICOM task 40 identified by the Task ID and corresponding to the destination remote device for that first job. As previously disclosed, a separate DICOM task is configured for each remote device having a page filled out on the Device Configuration menu. When the DICOM task 40 receives a job from the Active Queue, it will read the Image File Name field (i.e., the pointer), which will contain the file name of the image to be formatted and transferred to the destination remote device. The DICOM task 40 then retrieves the image from the named file on the hard disk and reformats it into the appropriate DICOM object in accordance with the instructions from the Attribute Control Engine 41. In addition to the pixel data for the image being transferred, the DICOM object constructed by the DICOM task will include attribute data in DICOM format. If the remote device is a storage device, the DICOM task will also attach a UID to the image.

Next the DICOM task 40 will open a connection (association) to the destination remote device and negotiate a syntax. In particular, the DICOM task 40 sends a request via the network manager 42 and a port 44 that an association with the configured remote device be opened. If the remote device responds affirmatively and if a communications syntax is agreed upon, the association is opened. Once the association is open and assuming that a channel on the network is available (i.e., the network is not busy), the image is sent from the imager onto the network, again via network manager 42 and port 44. If the destination remote device sends back a message that the image transfer was successful, then the DICOM task 40 notifies the queue manager 38. The queue manager then removes the entry for the successfully transferred image from the Active Queue and deletes that image file from the hard disk 36. If the message from the destination remote device indicates that the image transfer was unsuccessful, then the queue manager 38 moves the entry for the unsuccessfully transferred image from the Active Queue to a Holding Queue and does not delete that image file from the hard disk 36. The Holding Queue is also a linked list of elements maintained both on the hard disk and in system memory. The same procedure applies when transferring a film session of multiple images to a remote printer, except that the element for the multi-image film session will be transferred to the Holding Queue unless all of the images making up the film session are transferred successfully.

Figure 5:
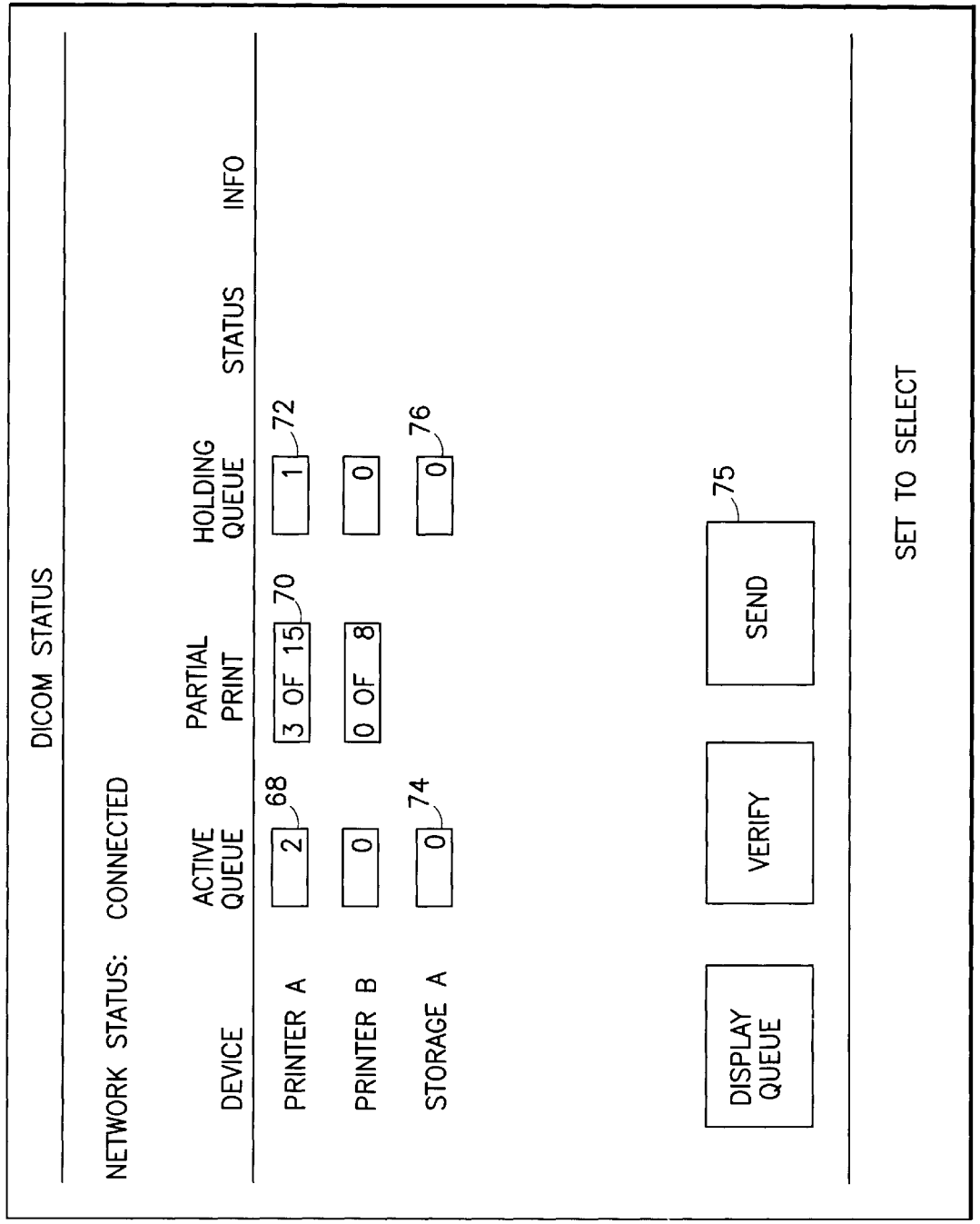
FIG. 5 is a schematic reproducing a "DICOM Status" menu which can be called up on the display monitor to check the status of images in the imager which are waiting to be sent on the DICOM network in accordance with the preferred embodiment.

In response to a view menu instruction inputted via the operator interface 22, the DICOM queue manager causes the display monitor 18 to display a DICOM status menu having entries for each remote device with queued jobs. Each entry on the status menu includes respective fields for indicating the number of jobs in the Active Queue, the number of jobs in the Holding Queue, and the number of image files in the Partial Print Queue which are directed to that particular remote device. An exemplary DICOM status menu, listing activated Printers A and B and activated Storage A, is shown in FIG. 5. The DICOM status menu includes an Active Queue field 68 and a Holding Queue field 72, as well as a Partial Print field 70 for each activated printer configured to print multi-image film sessions. The DICOM status menu also includes an Active Queue field 74 and a Holding Queue field 76 for each activated remote device configured to receive images singly (e.g., storage devices). The Active Queue field for each remote device indicates the number of jobs held in the Active Queue which are destined to be sent to that particular remote device, while the Holding Queue field indicates the number of failed jobs held in the Holding Queue and destined for that same remote device. A "job" may comprise a single image or multiple images. The Partial Print field, on the other hand, indicates the number of image files which have been acquired for constructing a particular film session (i.e., the number of image files named in the Image File Name field 90 in FIG. 7 of the corresponding list element) and the total number of image files constituting a full or complete film session for a particular printer. Since the storage devices handle single images, not multi-image film sessions, the DICOM status menu shows Partial Print fields only for printing devices.

Although the preferred embodiment employs double-linked lists, persons skilled in the art will readily appreciate that data structures other than lists (e.g., tree structures) can be used to virtually represent a queue of images. In addition, although the preferred embodiment uses separate lists for the active queue, partial print queue and holding queue, all elements could be organized in a single list, with each element having an attribute to indicate to which of the three queues the element belongs.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An imaging system comprising:
   a networking port for communicating with first and second remote devices on a network; and
   an image acquisition subsystem;
   memory storing acquired frames of image data in respective image files and storing first and second sets of attribute data in first and second attribute control files respectively, said first and second sets of attribute data corresponding to said first and second remote devices respectively; and
   first and second object constructing tasks for constructing data objects with data from said image files and attribute data from said first and second attribute control files respectively, said first object constructing task being configured to construct data objects acceptable to said first remote device and said second object constructing task being configured to construct data objects acceptable to said second remote device;
   an attribute control engine which communicates said first set of attribute data to said first object constructing task and which communicates said second set of attribute data to said second object constructing task, whereby said first object constructing task constructs data objects with said first set of attribute data and said second object constructing task constructs data objects with said second set of attribute data; and
   means for transferring data objects from said first and second object constructing tasks to said networking port.

2. The system as recited in claim 1, wherein said memory comprises a hard disk and system memory, wherein said first and second attribute control files are read from said hard disk and written into said system memory by said attribute control engine during powering up of said system.

3. The system as recited in claim 2, further comprising a third set of attribute data in a default attribute control file stored on said hard disk, wherein said first and third sets of attribute data are substantially the same.

4. The system as recited in claim 1, wherein said first and second sets of attribute data are different.

5. The system as recited in claim 1, wherein said first object constructing task queries said attribute control engine during construction of an data object, said attribute control engine reading attribute data from said first attribute control file in response to said queries.

6. The system as recited in claim 5, wherein said first set of attribute data comprises storage attribute data and printing attribute data, and said first object constructing task queries said attribute control engine concerning said storage attribute data but not said printing attribute data in said first set of attribute data when said first remote device is a storage device, and queries said attribute control engine concerning said printing attribute data but not said storage attribute data in said first set of attribute data when said first remote device is a printer.

7. An imaging system comprising:
   a networking port for communicating with first and second remote devices on a network; and
   an image acquisition subsystem;
   memory storing acquired frames of image data in respective image files and storing first and second sets of attribute data in first and second attribute control files respectively, said first and second sets of attribute data corresponding to said first and second remote devices respectively; and
   a computer programmed to perform the following steps:
   (a) retrieving first and second image files from said memory;
   (b) constructing a first data object with data from a first image file and first attribute data read from said first attribute control file, said first data object having a format compatible with said first remote device;
   (c) constructing a second data object with data from a second image file and second attribute data read from said second attribute control file, said first data object having a format compatible with said second remote device; and
   (d) transferring said first and second data objects to said networking port.

8. The system as recited in claim 7, wherein said memory comprises a hard disk, and said computer is further programmed to read said first and second attribute control files from said hard disk during powering up of said system.

9. The system as recited in claim 8, further comprising a third set of attribute data in a default attribute control file stored on said hard disk, wherein said first and third sets of attribute data are substantially the same.

10. The system as recited in claim 7, wherein said first and second sets of attribute data are different.

11. An imaging system comprising:
a networking port for communicating with first and second remote devices on a network; and
an image acquisition subsystem;
memory storing acquired frames of image data in respective image files and storing first and second sets of attribute data in first and second attribute control files respectively, said first and second sets of attribute data corresponding to said first and second remote devices respectively;
an operator interface; and
a computer programmed with first and second configurable tasks, and further programmed to perform the following steps:
(a) storing first and second sets of device configuration data inputted via said operator interface in said memory, said first and second sets of device configuration data corresponding to said first and second remote devices respectively;
(b) configuring said first and second configurable tasks in accordance with said first and second sets of device configuration data, whereby said configured first configurable task will construct data objects with data from said image files and with said first set of attribute data, and said configured second configurable task will construct data objects with data from said image files and with said second set of attribute data; and
(c) transferring data objects from said configured first and second configurable tasks to said networking port.

12. The system as recited in claim 11, wherein said computer is further programmed with an attribute control engine which communicates said first set of attribute data to said configured first configurable task and which communicates said second set of attribute data to said configured second configurable task, whereby said configured first configurable task constructs data objects with said first set of attribute data and said configured second configurable task constructs data objects with said second set of attribute data.

13. The system as recited in claim 12, wherein said configured first configurable task queries said attribute control engine during construction of an data object, said attribute control engine reading attribute data from said first attribute control file in response to said queries.

14. The system as recited in claim 13, wherein said first set of attribute data comprises storage attribute data and printing attribute data, and said configured first configurable task queries said attribute control engine concerning said storage attribute data but not said printing attribute data in said first set of attribute data when said first set of device configuration data indicates that said first remote device is a storage device, and queries said attribute control engine concerning said printing attribute data but not said storage attribute data in said first set of attribute data when said first set of device configuration data indicates that said first remote device is a printer.

15. An imaging system comprising:
a networking port for communicating with first and second remote devices on a network; and
an operator interface;
an image acquisition subsystem;
memory storing acquired frames of image data in respective image files and storing first and second sets of attribute data in first and second attribute control files respectively, said first and second sets of attribute data corresponding to said first and second remote devices respectively; and
first and second configurable tasks for constructing data objects with data from said image files and attribute data from said attribute control files;
means for configuring said first and second configurable tasks in accordance with first and second sets of device configuration data inputted via said operator interface, said first and second sets of device configuration data corresponding to said first and second remote devices respectively;
an attribute control engine which communicates said first set of attribute data to said configured first configurable task and which communicates said second set of attribute data to said configured second configurable task, whereby said configured first configurable task constructs data objects with said first set of attribute data and said configured second configurable task constructs data objects with said second set of attribute data; and
means for transferring data objects from said configured first and second configurable tasks to said networking port.

16. A method of operating a computerized imaging system, comprising the steps of:
connecting a networking port of said imaging system to a network having first and second remote devices connected thereto;
storing first and second attribute control files containing first and second sets of attribute data corresponding to first and second remote devices respectively, said first and second sets of attribute data being different;
storing first and second frames of image data in first and second image files respectively;
constructing a first data object with data from a first image file and first attribute data read from said first attribute control file, said first data object having a format compatible with said first remote device;
constructing a second data object with data from a second image file and second attribute data read from said second attribute control file, said first data object having a format compatible with said second remote device; and
transferring said first and second data objects to said networking port.

17. The method as recited in claim 16, wherein first set of attribute data comprises storage attribute data and printing attribute data, and said step of constructing a first data object comprises the step of reading said storage attribute data but not said printing attribute data in said first set of attribute data when said first remote device is a storage device, and comprises the step of reading said printing attribute data but not said storage attribute data in said first set of attribute data when said first remote device is a printer.

18. A method of reprogramming a computerized imaging system, comprising the steps of:
writing a first set of attribute data into a first attribute control file on a hard disk during initial programming, said first attribute control file being read only;
writing a second set of attribute data into a second attribute control file on said hard disk during initial programming, said second attribute control file being programmable, and said first and second sets of attribute data being substantially the same;

connecting said imaging system to a network having a remote device connected thereto, said remote device being configured to require a predetermined set of attribute data;

determining that said second set of attribute data is incompatible with said predetermined set of attribute data;

writing a third set of attribute data into said second attribute control file in place of said second set of attribute data, said third set of attribute data being compatible with said predetermined set of attribute data;

acquiring image data;

constructing a data object from said image data and said third set of attribute data; and sending said data object to said remote device via said network.

19. The method as recited in claim 18, further comprising the step of reading said first set of attribute data from said first attribute control file and writing said first set of attribute data into said second attribute control file in place of said third set of attribute data.

20. A method for constructing a DICOM object in an imaging system, comprising the steps of:

identifying a remote device destined to receive a DICOM object, said remote device accepting only DICOM objects having a predetermined set of attribute data;

retrieving an attribute control file containing at least said predetermined set of attribute data;

acquiring a frame of image data;

incorporating said frame of image data in said DICOM object;

for each attribute datum in said attribute control file, determining whether said attribute datum belongs to said predetermined set of attribute data; and for each attribute datum belonging to said attribute control file, determining a value and a tag number of said attribute; and incorporating said value and said tag number for each attribute datum belonging to said attribute control file in said DICOM object.

* * * * *